(12) United States Patent
Voic

(10) Patent No.: US 9,211,137 B2
(45) Date of Patent: Dec. 15, 2015

(54) ULTRASONIC CUTTING BLADE WITH COOLING LIQUID CONDUCTION

(71) Applicant: Misonix Incorporated, Farmingdale, NY (US)

(72) Inventor: Dan Voic, Cedar Grove, NJ (US)

(73) Assignee: MISONIX, INCORPORATED, Farmingdale, NY (US)

( * ) Notice: Subject to any disclaimer, the term of this patent is extended or adjusted under 35 U.S.C. 154(b) by 274 days.

(21) Appl. No.: 13/930,170

(22) Filed: Jun. 28, 2013

(65) Prior Publication Data

US 2015/0005775 A1 Jan. 1, 2015

(51) Int. Cl.
*A61B 17/16* (2006.01)
*A61B 17/32* (2006.01)
*A61B 17/14* (2006.01)

(52) U.S. Cl.
CPC ....... *A61B 17/320068* (2013.01); *A61B 17/141* (2013.01); *A61B 2017/1651* (2013.01); *A61B 2017/320004* (2013.01); *A61B 2017/320072* (2013.01); *A61B 2017/320084* (2013.01); *A61B 2217/007* (2013.01)

(58) Field of Classification Search
CPC ........... A61B 17/320068; A61B 2017/320084; A61B 2017/320072; A61B 2017/320076; A61B 2017/32008
See application file for complete search history.

(56) References Cited

U.S. PATENT DOCUMENTS

| | | | | |
|---|---|---|---|---|
| 3,433,226 A * | 3/1969 | Boyd | | 606/159 |
| 3,805,787 A * | 4/1974 | Banko | | 604/22 |
| 4,832,683 A * | 5/1989 | Idemoto et al. | | 604/22 |
| 4,869,715 A * | 9/1989 | Sherburne | | 604/22 |
| 5,084,009 A * | 1/1992 | Mackool | | 604/22 |
| 5,151,083 A * | 9/1992 | Pichler | | 604/22 |
| 5,163,433 A * | 11/1992 | Kagawa et al. | | 601/2 |
| 5,188,102 A * | 2/1993 | Idemoto et al. | | 604/22 |
| 5,261,922 A * | 11/1993 | Hood | | 606/167 |
| 5,286,256 A * | 2/1994 | Mackool | | 604/22 |
| 5,346,502 A * | 9/1994 | Estabrook et al. | | 606/169 |
| 5,354,265 A * | 10/1994 | Mackool | | 604/22 |
| 5,382,251 A * | 1/1995 | Hood et al. | | 606/99 |
| 5,462,522 A * | 10/1995 | Sakurai et al. | | 604/22 |
| 5,484,398 A * | 1/1996 | Stoddard | | 604/22 |
| 5,702,360 A * | 12/1997 | Dieras et al. | | 604/22 |
| 5,728,130 A * | 3/1998 | Ishikawa et al. | | 606/185 |
| 5,772,627 A * | 6/1998 | Acosta et al. | | 604/22 |
| 5,879,363 A * | 3/1999 | Urich | | 606/167 |
| 6,117,151 A * | 9/2000 | Urich et al. | | 606/169 |
| 6,117,152 A * | 9/2000 | Huitema | | 606/169 |
| 6,254,622 B1 * | 7/2001 | Hood | | 606/169 |
| 6,379,371 B1 * | 4/2002 | Novak et al. | | 606/169 |
| 6,443,969 B1 | 9/2002 | Novak et al. | | |
| 6,592,541 B1 * | 7/2003 | Kurwa | | 604/22 |
| 2002/0077550 A1 * | 6/2002 | Rabiner et al. | | 600/439 |
| 2002/0077644 A1 * | 6/2002 | Beaupre | | 606/169 |

(Continued)

*Primary Examiner* — Christian Sevilla
(74) *Attorney, Agent, or Firm* — R. Neil Sudol; Henry D. Coleman

(57) ABSTRACT

An ultrasonic surgical blade has a blade body at a distal end and a shank at a proximal end, the shank being connectable at a proximal end to a source of ultrasonic mechanical vibrations. A sheath surround at least a portion of the shank. The sheath is configured to define a space between an outer surface of the shank and an inner surface of the sheath. The shank is provided with a liquid-conducting channel terminating in at least one outlet at the outer surface of the shank to enable delivery of irrigant to the space between the shank and the sheath for eventual conduction along an outer surface of the blade body.

14 Claims, 1 Drawing Sheet

(56) References Cited

U.S. PATENT DOCUMENTS

| | | | |
|---|---|---|---|
| 2002/0103438 A1* | 8/2002 | Cronin et al. | 600/459 |
| 2002/0103497 A1* | 8/2002 | Satou | 606/169 |
| 2003/0040672 A1* | 2/2003 | Ogura et al. | 600/437 |
| 2003/0060736 A1* | 3/2003 | Martin et al. | 601/2 |
| 2003/0163131 A1* | 8/2003 | Manna et al. | 606/50 |
| 2004/0030254 A1* | 2/2004 | Babaev | 600/459 |
| 2005/0177184 A1* | 8/2005 | Easley | 606/167 |
| 2005/0273127 A1* | 12/2005 | Novak et al. | 606/169 |
| 2006/0235305 A1* | 10/2006 | Cotter et al. | 600/459 |
| 2006/0241470 A1 | 10/2006 | Novak et al. | |
| 2007/0060926 A1* | 3/2007 | Escaf | 606/107 |
| 2008/0009848 A1 | 1/2008 | Paraschiv et al. | |
| 2008/0015551 A1* | 1/2008 | Feine | 606/1 |
| 2008/0058775 A1* | 3/2008 | Darian et al. | 606/1 |
| 2008/0194999 A1* | 8/2008 | Yamaha et al. | 601/2 |
| 2008/0208231 A1* | 8/2008 | Ota et al. | 606/169 |
| 2009/0143795 A1* | 6/2009 | Robertson | 606/169 |
| 2010/0057118 A1* | 3/2010 | Dietz et al. | 606/169 |
| 2010/0106173 A1* | 4/2010 | Yoshimine | 606/169 |
| 2011/0125174 A1* | 5/2011 | Babaev | 606/169 |
| 2014/0276469 A1* | 9/2014 | Greep et al. | 604/264 |
| 2015/0025451 A1* | 1/2015 | Banko | 604/35 |
| 2015/0057692 A1* | 2/2015 | Voic | 606/169 |

* cited by examiner

ULTRASONIC CUTTING BLADE WITH COOLING LIQUID CONDUCTION

FIELD OF THE INVENTION

This invention relates to an ultrasonic tool. More particularly, this invention relates to an ultrasonic cutting blade. The blade is particularly useful in a surgical application to cut tissue such as cartilage and bone. The present invention is also directed in part to an associated surgical method.

BACKGROUND OF THE INVENTION

In the field of orthopedics, the cutting of living bone is a prerequisite for many procedures. Such procedures include the reconstruction of damaged tissue structures due to accidents, the grafting of healthy bone into areas damaged by disease, or the correction of congenital facial abnormalities like a receding chin line. Over several centuries, these tasks were performed through the utilization of devices called bone saws.

Traditional bone saws are categorized into several basic categories. Hand powered saws or drills are just that, hand held devices which require the operator to move the device in a fashion similar to that used for carpentry tools. Powered devices, whether electric or pneumatic, are of either the reciprocating or rotary type. The reciprocating devices use a flat, sword like blade where the back and forth motion is provided by a motor instead of the hand. The rotary devices use a rotating motor to spin a drill bit or a blade that has teeth arranged around its circumference similar to a table saw blade. All of these traditional bone saws are used today in medical procedures around the world.

While traditional saws are functional, they have many disadvantages. With either the band or reciprocating saws, for instance, it is not easy to initiate and direct a cut. A cut must start from an edge or, alternatively, a starting hole must be used. To create a starting hole, a drill or similar instrument is operated to bore into the bone. Subsequently, a cutting blade is inserted into the bored hole. The user can then proceed to cut. Alternatively, a rotary type blade may be used. However, when a rotary blade is used, the cut must follow a relatively straight path to prevent the blade from binding in the cut. With all blades the ability to create a curved or compound angle cut is extremely limited by the blade chosen. The relatively thick blades have a wide kerf, so that a significant thickness of the viable bone is lost in the cutting procedure. Physicians would like this width to be as thin as possible in most procedures where reconstruction is necessary.

Above all, the relatively slow linear or tangential speeds of conventional bone saw blades coupled with the teeth necessary for cutting result in high frictional losses, which becomes manifested as heat. Heat will cause necrosis of the tissue if the bone temperatures reach 47° C. for more than a few seconds. When tissue necroses, the bone recedes after the surgery as the necrotic bone is overgrown. During such natural post-surgical tissue developments, the thickness of the cuts in the bone actually increases. The bone rescission process must be complete before healing can begin. To prevent the shortening of the length of the bone, metal plates and screws are used to fix the bone fragments in proper position. All of these factors obviously lead to increased operative time, and more importantly, to dramatically increased healing time, since the bone must knit across a greater span. Some studies have shown the strength of the bone to be effected negatively as well When an upper or lower jaw is to be cut in elective surgery, the heating effect of traditional saws requires even more extraordinary intervention to prevent damage. Cutting the jaw between the teeth will cause loss of teeth if the bone is damaged or does not heal quickly. To prevent the tooth loss, the teeth must be spread apart preoperatively; sometimes forcing the patient to wear braces for up to 6 months before the operation can take place. In these cases, the costs and patient discomfort increases dramatically.

To limit the tissue temperature rise in an attempt to reduce necrosis, some traditional surgical saws provide cooling liquid to the surgical site. See, for instance, U.S. Pat. No. 4,008,720 to Brinckmann et al. These devices typically introduce coolant into spaces between segments on the cutting edge or rely on spray methods to flood the cutting site with fluid. Another technique employed by clinicians is to make very light cuts and increase the time between passes of the tool. Coupled with irrigation of the area, bone temperature rise is reduced measurably. Of course, this technique increases operative time and clinician fatigue.

Several researchers have proposed the use of ultrasonic tools for bone separation. The use of ultrasonic surgical instruments for cutting through various tissues is well known. While these devices are superior to the traditional saws in several aspects such as reduced kerf size, reduced noise, and superior ability for making complex geometric cuts, the temperature rise in bone due to frictional heating at the blade/tissue interface is still a significant problem. The problem is exacerbated with the use of ultrasonics due to the rapid motion involved as compared to that of traditional reciprocating saws. Some designers have tried to reduce heating by modifying the cross-section of the cutting blade. U.S. Pat. No. 5,188,102 to Idernoto, U.S. Pat. No. 4,188,952 to Loschilov, and U.S. Pat. No. 5,261,922 to Hood all show designs for cutting which have modified cross sections to reduce frictional heating.

Several ultrasonic devices have provided cooling to the cutting blade with varied degrees of success. U.S. Pat. No. 4,823,790 to Alperovich et al. shows a design for a cryogenically cooled scalpel blade. However, this design may actually damage viable tissue by freezing. In addition, this design does not provide any coolant to surrounding tissue not in direct contact with the blade.

U.S. Pat. Nos. 5,205,817, 5,188,102, and 4,832,683 all to Idemoto show examples of ultrasonic instruments with provisions for fluid cooling. These instruments, however, either do not provide optimal coolant flow where it is needed, mainly at the cutting portion of the blade, or for ones that do provide coolant at the tip, they interrupt the cutting edge with holes for the coolant. An interrupted, uneven cutting edge hinders manipulation and makes it difficult to guide the blade on the bone surface.

One phenomenon associated with ultrasonic tooling which acts to hinder the beneficial effects of irrigating the operative site is ultrasonic atomization. When an ultrasonically vibrating body is brought into contact with fluid, that fluid is broken into small droplets, which have a size inversely proportional to the frequency of vibration. In other words, the higher the frequency, the smaller and more mobile the liquid drop. Droplets created by ultrasonic vibrations can be very small in size, with some being less than 1 micron in diameter. This phenomenon is well known to the art. In fact, many devices intended to atomize liquid, such as room humidifiers, medical nebulizers, and industrial spray nozzle are based upon this principle. In the operating theater, however, the presence of nebulized particles is not appreciated, since these particles may contain viral or bacterial agents. Also, some of the fluid will be atomized before reaching the operative site, reducing the cooling efficiency. An effective way to insure the liquid transport is needed.

U.S. Pat. No. 6,379,371 discloses an ultrasonic surgical blade with cooling, which has a blade body with a smooth continuous cutting edge and a shank connected at one end to the blade body and operatively connectable at an opposite end to a source of ultrasonic vibrations. The shank is provided with an axially extending bore for the conveyance of cooling fluid to the cutting edge, while the blade body is provided with an axially extending through-slot communicating at one end with the bore. The blade body is preferably provided at an end opposite the shank with a recess communicating, with the bore for distributing fluid from the slot towards the cutting edge. The recess may have a configuration that parallels at least a portion of the cutting edge. Where the cutting edge is circular and the blade body has a planar surface between the fluid distribution guide surface and the cutting edge, for instance, the recess has a fluid distribution surface inclined with respect to the planar blade surface and extending along a circular arc.

SUMMARY OF THE INVENTION

The present invention aims to provide an improved ultrasonic tool or probe which has an improved cooling capability. An ultrasonic tool or probe in accordance with the invention may particularly take the form of ultrasonic cutting blade which allows thin kerf cuts, does not require predrilled holes for cutting, allows complex geometric cuts, has a continuous cutting surface, and provides for liquid irrigation at primarily the blade/tissue interface. More specifically, the present invention pertains to an ultrasonically vibrated cutting blade with an improved provision for delivery of a cooling medium for reducing and limiting thermal damage to living tissue. The present invention specifically targets the application of cutting viable bones in surgery, although the device is not exclusive to this application.

An ultrasonic surgical device comprises, in accordance with the present invention, a blade having a blade body at a distal end and a shank at a proximal end, the shank being connectable at a proximal end to a source of ultrasonic mechanical vibrations. The device further comprises a sheath surrounding at least a portion of the shank. The sheath is configured to define a space between an outer surface of the shank and an inner surface of the sheath. The shank is provided with a liquid-conducting channel terminating in at least one outlet at the outer surface of the shank to enable delivery of irrigant to the space between the shank and the sheath for eventual conduction along an outer surface of the blade body.

The shank of the blade is geometrically distinguishable from the blade body. Hence the liquid outlet is disposed proximally or upstream of the blade body. Typically, the shank has a transverse dimension which is substantially larger than a characteristic transverse dimension of the blade body. In other words, the blade body is thin relative to the shank. The shank includes a shank body at a proximal end and a tapered distal end portion connected to the blade body, the liquid outlet being located in the tapered portion of the shank.

Pursuant to further features of the present invention, the sheath includes a tapered segment over the tapered portion of the shank and the sheath terminates proximate a proximal end of the blade body. The sheath may extend only over the shank, including the tapered portion thereof. Alternatively, the sheath may have a distal end portion or skirt that is coextensive only with a most proximal portion of the blade body.

In an ultrasonic bone-cutting blade in accordance with the present invention, the blade body is flattened or planar. The shank body is typically cylindrical, so that the tapered portion converges from a cylindrical shape at a proximal end to a flattened shape at a distal end.

Pursuant to additional features of the present invention, the outlet is one of at least two outlets, the tapered portion of the shank has a pair of sloped surfaces inclined relative to the longitudinal axis of the blade ad disposed at an angle relative to one another, and the channel includes a central or axial upstream section and at least two downstream sections branching from the upstream section to respective outlets disposed in respective sloping surfaces of the tapered shank portion.

DETAILED DESCRIPTION

Figure 1:
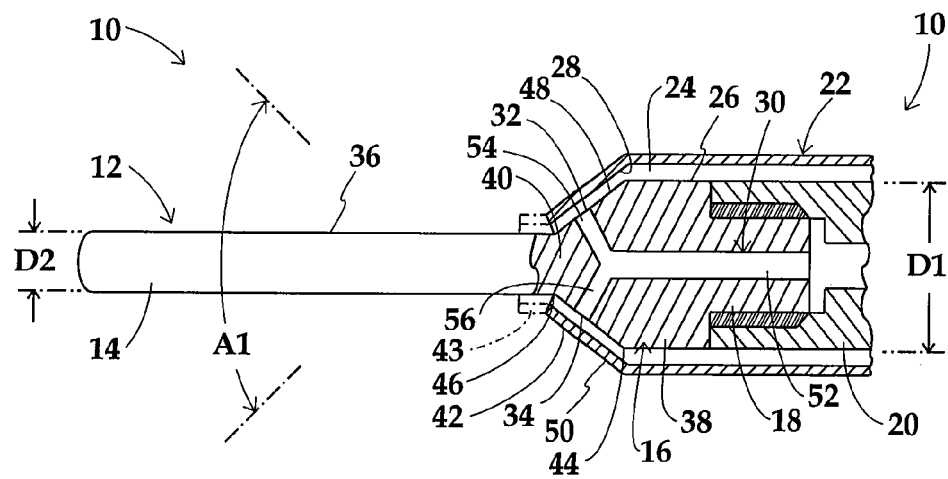
FIG. 1 is a schematic longitudinal cross-sectional view of an ultrasonic surgical tool in accordance with the present invention.

As illustrated in FIG. 1, an ultrasonic surgical device or assembly 10 comprises a blade 12 having a blade body 14 at a distal end and a shank 16 at a proximal end. Shank 16 is provided at a proximal end with an externally threaded screw-type connector 18 for connecting blade 12 to a source of ultrasonic mechanical vibrations (not separately shown) in a handpiece 20.

Device or assembly 10 further comprises a sheath 22 that surrounds at least a portion of shank 16. Sheath 22 is configured to define a space 24 between an outer surface 26 of shank 16 and an inner surface 28 of the sheath. Shank 16 is provided with a liquid-conducting channel 30 terminating in at least one outlet 32 and preferably multiple outlets 32 and 34 at outer surface 26 of shank 16 to enable delivery of irrigant to space 24 between the shank and sheath 22 for eventual conduction along an outer surface 36 of blade body 14.

Shank 16 has a transverse dimension D1 which is substantially larger than a characteristic transverse dimension D2 of blade body 14. Inasmuch as blade body 14 is thin relative to shank 16, the shank naturally includes a shank body 38 at a proximal end and a tapered distal end portion 40 connected to blade body 14. Liquid outlets 32 and 34 are located in tapered portion 40 of shank 16.

Sheath 22 includes a tapered segment 42 that is disposed over tapered portion 40 of shank 16. Sheath 22 terminates proximate a proximal end of blade body 14. Sheath 22 may extend only over shank 16, including tapered portion 40 thereof, as shown. Alternatively, sheath 22 may have a distal end portion 43 coextensive with and disposed over a proximal portion of blade body 14.

Blade body 14 is flattened or planar for use as a bone-cutting blade. Shank body 38 is typically cylindrical, so that tapered portion 40 converges from a cylindrical shape at a proximal end 44 to a flattened shape at a distal end 46.

Tapered portion 40 of shank 16 has a pair of sloping or inclined planar surfaces 48 and 50 disposed at an acute angle A1 relative to one another. Channel 30 includes a central or axial upstream section 52 and at least two downstream sections 54 and 56 branching from the upstream section to respective outlets 32 and 34 disposed in respective planar surfaces 48 and 50 of tapered shank portion 40.

Figure 2:
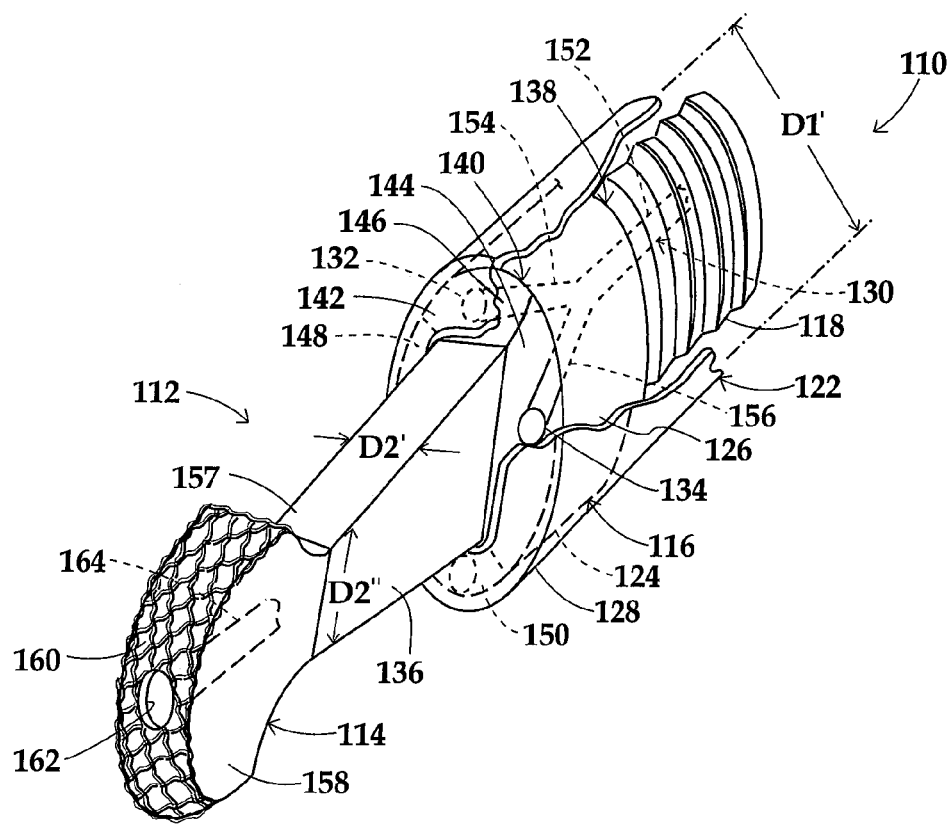
FIG. 2 is a schematic perspective view of another ultrasonic surgical tool in accordance with the present invention.

FIG. 2 illustrates an ultrasonic surgical device or assembly 110 that comprises a blade 112 having a blade body 114 at a distal end and a shank 116 at a proximal end. Shank 116 is provided at a proximal end with an externally threaded screw-type connector 118 for connecting blade 112 to a source of ultrasonic mechanical vibrations (not separately shown).

Device or assembly 110 further comprises a sheath 122 that surrounds at least a portion of shank 116. Sheath 122 is configured to define a space 124 between an outer surface 126 of shank 116 and an inner surface 128 of the sheath. Shank 116 is provided with a liquid-conducting channel 130 terminating in at least one outlet 132 and preferably multiple outlets 132, 134 at outer surface 126 of shank 116 to enable delivery of irrigant to space 124 between the shank and sheath 122 for eventual conduction along outer surfaces 136 of blade body 114.

Shank 116 has a transverse dimension D1' which is substantially larger than a characteristic transverse dimension D2' (and D2") of blade body 114. Inasmuch as blade body 114 is thin relative to shank 116, the shank naturally includes a shank body 138 at a proximal end and a tapered distal end portion 140 connected to blade body 114. Liquid outlets 132, 134 are located in tapered portion 140 of shank 116.

Sheath 122 includes a tapered segment 142 that is disposed over tapered portion 140 of shank 116. Sheath 122 terminates proximate a proximal end of blade body 114. Sheath 122 may extend only over shank 116, including tapered portion 140 thereof, as shown. Alternatively, sheath 122 may have a distal end portion (not shown) coextensive with and disposed over a proximal portion of blade body 114.

Tapered portion 140 of shank 116 has four sloping or inclined surfaces 144, 146, 148 and 150, disposed in opposing pairs 144, 148 and 146, 150 with members of each pair being perforated by respective fluid outlets 134 and 132. Channel 130 includes a central or axial section 152 and pairs of branching sections 154, 156 extending from the central section to respective outlets 132, 134.

Blade body 114 includes a tapered shaft 157 and a head 158 that is flattened in one dimension and enlarged in a second, perpendicular dimension. Head 158 is provided with an operative knurled cutting surface 160 that is convex and, more particularly, a cylindrical section. Blade body 114 is provided with an axial bore 164 that is coaxial and continuous with channel 130 and that terminates in an outlet or port 162 in cutting surface 160 for delivering liquid coolant to the cutting surface.

Blade body 114 has an active length measured from the distal end of shank 116, and more particularly from the distal edges of sloped surfaces 144, 146, 148, 150, to the distal most point of operative surface 160. The active length is exemplarily between 25 and 40 mm. Head 158 is enlarged in one direction (vertical direction in the drawing). In that direction blade head 158 is longer than or equal to the width of blade body 114 at the proximal end, i.e., longer than or equal to the distance between the distal edges (not separately designated) of sloped surfaces 146 and 150.

Sheaths 22 and 122 stop the formation of a cloud of atomized liquid that would tend to obstruct the field of view. Sheaths 22 and 122 facilitate the delivery of irrigant along the lateral surfaces of blade bodies 14 and 114, at the tissue interface. The irrigant or liquid serves to cool the tissue at the interface and prevent undue tissue burning.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An ultrasonic surgical device comprising:
   a blade having a blade body at a distal end and a shank at a proximal end, said shank being connectable at a proximal end to a source of ultrasonic mechanical vibrations; and
   a sheath surrounding at least a portion of said shank, said sheath defining a space between an outer surface of said shank and an inner surface of said sheath,
   said shank being provided with a liquid-conducting channel terminating in at least one outlet at said outer surface to enable delivery of irrigant to said space for conduction along an outer surface of said blade body.

2. The surgical device of claim 1 wherein said blade body has a first transverse dimension, said shank having a second transverse dimension substantially larger than said first transverse dimension.

3. The surgical device of claim 2 wherein said shank includes a shank body at a proximal end and a tapered distal end portion connected to said blade body, said at least one outlet being located in said tapered portion.

4. The surgical device of claim 3 wherein said sheath includes a tapered segment over said tapered portion of said shank.

5. The surgical device of claim 4 wherein said sheath terminates proximate a proximal end of said blade body.

6. The surgical device of claim 5 wherein said blade body is flattened or planar.

7. The surgical device of claim 6 wherein said shank body is cylindrical, said tapered portion converging from a cylindrical shape at a proximal end to a flattened shape at a distal end.

8. The surgical device of claim 7 wherein said at least one outlet is one of at least two outlets, said tapered portion having a pair of sloped surfaces disposed at an angle relative to one another, said channel including a central or axial upstream section and at least two downstream sections branching from said upstream section to respective ones of said outlets disposed in respective ones of said sloped surfaces.

9. The surgical device of claim 1 wherein said blade body is flattened or planar.

10. The surgical device of claim 9 wherein said shank includes a cylindrical shank body and a tapered portion converging from a cylindrical shape at a proximal end to a flattened shape at a distal end.

11. The surgical device of claim 1 wherein said at least one outlet is one of at least two outlets disposed on opposing sides of said shank, said channel including a central or axial upstream section and at least two downstream sections branching from said upstream section to respective ones of said outlets.

12. The surgical device of claim 1 wherein said sheath terminates proximate a proximal end of said blade body.

13. A surgical method comprising:
   providing an ultrasonic surgical tool having a blade body and a shank connected at a proximal end thereof, said blade body having an operative surface or edge, said shank being formed with a channel extending to an outlet at an outer surface of said shank;
   operatively connecting a proximal end of said shank to a source of ultrasonic mechanical vibrations;
   operatively coupling said channel to a source of liquid;
   moving said blade body to a surgical site on a patient;

placing said operative surface or edge in contact with organic tissues at said surgical site;

while said operative surface or edge is in contact with the organic tissues, generating ultrasonic mechanical vibrations in said blade body, thereby ultrasonically vibrating said operative surface or edge;

while said operative surface or edge is in contact with the organic tissues and during the generating of the ultrasonic mechanical vibrations in said blade body, feeding liquid under pressure from said source of liquid into said channel and from said channel to said outlet and into a space between said outer surface of said shank and a sheath over said shank; and conducting liquid from said space over an outer surface of said blade body.

14. The method of claim 13 wherein the conducting of liquid over an outer surface of said blade body includes conducting the liquid over said operative surface or edge.

* * * * *